US00PP27405P2

(12) United States Plant Patent
van der Walt

(10) Patent No.: US PP27,405 P2
(45) Date of Patent: Nov. 22, 2016

(54) ***TULBAGHIA* PLANT NAMED 'SAVANNA LIGHTNING'**

(50) Latin Name: *Tulbaghia violacea*
Varietal Denomination: Savanna Lightning

(71) Applicant: Ivan van der Walt, Pretoria (ZA)

(72) Inventor: Ivan van der Walt, Pretoria (ZA)

(73) Assignee: Abrus Enterprise, Pretoria (ZA)

( * ) Notice: Subject to any disclaimer, the term of this patent is extended or adjusted under 35 U.S.C. 154(b) by 0 days.

(21) Appl. No.: 14/756,494

(22) Filed: Sep. 10, 2015

(51) Int. Cl.
*A01H 5/02* (2006.01)

(52) U.S. Cl.
USPC ..... Plt./263.1

(58) Field of Classification Search
USPC ..... Plt./263.1, 398
CPC ..... A01H 5/0205
See application file for complete search history.

*Primary Examiner* — Kent L Bell
(74) *Attorney, Agent, or Firm* — Audrey Charles

(57) ABSTRACT

A new and distinct cultivar of *Tulbaghia* plant named 'Savanna Lightning', characterized by its white-colored flowers with a yellow-orange corona, medium green-colored foliage, and moderately vigorous, upright-mounding growth habit, is disclosed.

1 Drawing Sheet

Latin name of genus and species of plant claimed: *Tulbaghia violacea.*

Variety denomination: 'Savanna Lightning'.

BACKGROUND OF THE INVENTION

The present invention relates to a new and distinct cultivar of *Tulbaghia* plant botanically known as *Tulbaghia violacea* and hereinafter referred to by the cultivar name 'Savanna Lightning'.

The new *Tulbaghia* cultivar is a naturally-occurring sport of a *Tulbaghia violacea* var. *maritima* breeding selection, not coded, not patented, characterized by its medium purple-colored flowers having a yellow corona, dark green-colored foliage, and vigorous, upright-mounding growth habit. The new cultivar was discovered as a whole plant and selected during the summer of 2002 in a controlled environment in Pretoria, South Africa.

Asexual reproduction of the new cultivar by division since the summer of 2003 in Pretoria, South Africa and Valley Center, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Savanna Lightning' as a new and distinct cultivar of *Tulbaghia* plant:

1. White-colored flowers with a yellow-orange corona;
2. Medium green-colored foliage; and
3. Moderately vigorous, upright-mounding growth habit.

Plants of the new cultivar differ from plants of the parent primarily in flower color, foliage color and growth vigor.

Of the many commercially available *Tulbaghia* cultivars, the most similar in comparison to the new cultivar is 'Fairy Snow', not patented. However, in comparison, plants of the new cultivar differ from plants of 'Fairy Snow' in at least the following characteristics:

1. Plants of the new cultivar have a perianth tube color different from plants of 'Fairy Snow'; and
2. Plants of the new cultivar have a different corona color than plants of 'Fairy Snow'.

*Tulbaghia* plant 'Hinetul1', U.S. Plant Pat. No. 25,293 was not found to be commercially available; however, based on plant patent data plants of the new cultivar differ from plants of 'Hinetul1' in at least the following characteristics:

1. Plants of the new cultivar have a flower color different from plants of 'Hinetul1'; and
2. Plants of the new cultivar have a leaf color different from plants of 'Hinetul1'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Savanna Lightning'. The plants were grown in one gallon containers for 13 months in a poly-greenhouse in Guadalupe, Calif.

DETAILED BOTANICAL DESCRIPTION

Figure 1:
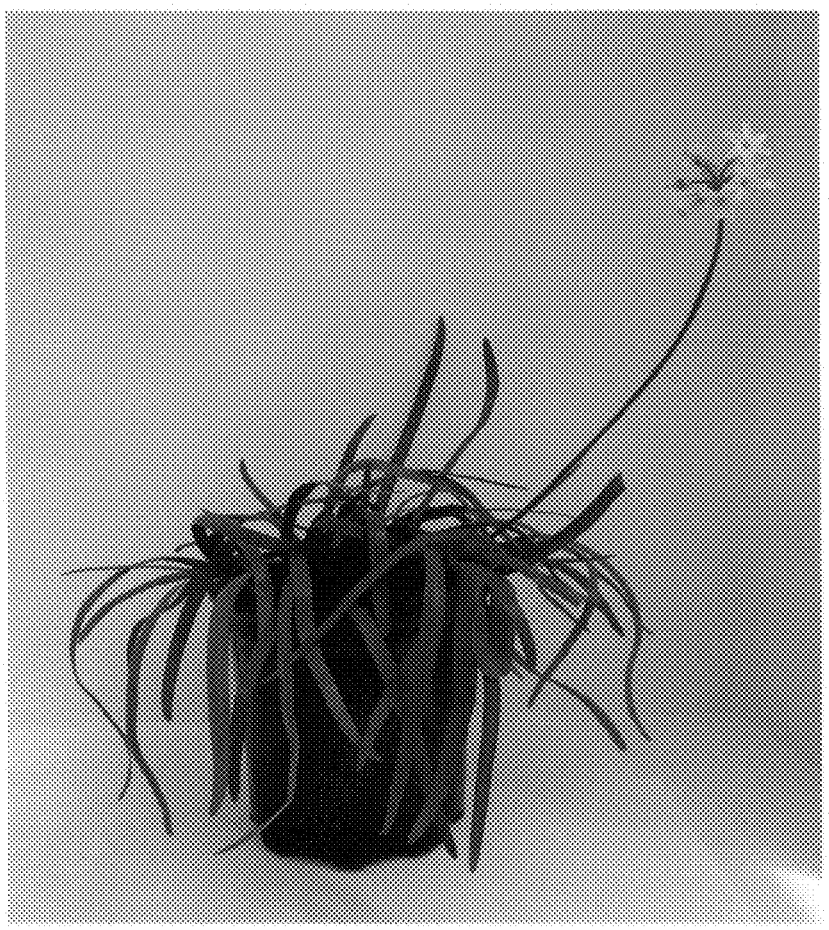
FIG. 1 illustrates a side view of the overall growth and flowering habit of 'Savanna Lightning'.
Figure 2:
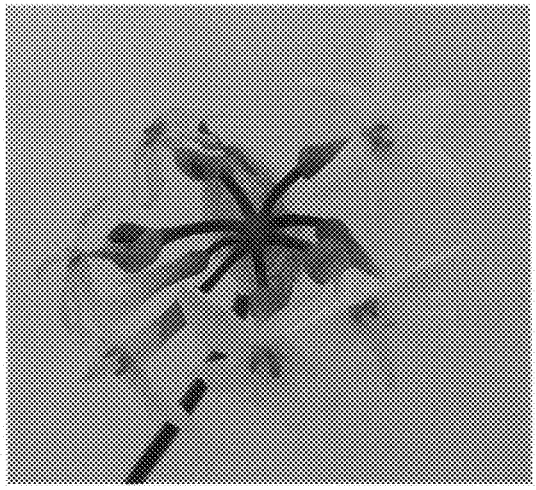
FIG. 2 illustrates a close-up view of an individual umbel of 'Savanna Lightning'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2015 under natural light conditions in West Chicago, Ill.

The following descriptions and measurements describe plants produced by division of stock plants and grown in a poly-covered greenhouse without supplemental heating or cooling. Temperatures for this period ranged from an average high of 75° F. (24° C.) to an average low of 52° F. (11° C.). The plants were grown in Guadalupe, Calif. in one gallon containers for approximately 13 months utilizing a soilless growth medium. Measurements and numerical values represent averages of typical plants.

Botanical classification: *Tulbaghia violacea* cultivar Savanna Lightning.

Parentage:

*Parent.*—A *Tulbaghia violacea* var. *maritima* breeding selection, not coded, not patented.

Propagation:

*Type.*—Divisions.

*Root description.*—Corm-like rhizome with thick roots white to light brown in color.

*Rooting habit.*—Freely branching.

Plant description:

*Commercial crop time.*—Approximately 52 to 60 weeks from a division to finish in a one-gallon container.

*Cold hardiness.*—To USDA Zone 7.

*Growth habit and general appearance.*—Moderately vigorous, upright-mounding, clumps of arching leaves and flowering stalks.

*Size.*—Height from soil level to top of plant plane: Approximately 26.0 cm. Height from soil level to top of foliage: Approximately 19.0 cm. Width: Approximately 37.0 cm.

*Branching habit.*—No branching, basal rosettes of leaves. Number of clumps per pot: Approximately 2. Number of rosettes per clump: Approximately 3.

Foliage description:

*General description.*—Quantity of leaves per rosette: Approximately 8. Fragrance: Strong garlic-scented when leaves bruised. Form: Simple. Arrangement: 2-ranked.

*Leaves.*—Aspect: Emerging leaves erect, then cascade. Shape: Linear. Margin: Entire. Apex: Broadly acute. Base: Sessile, sheathed. Venation pattern: Parallel. Length of mature leaf: Approximately 27.0 cm. Width of mature leaf: Approximately 1.2 cm. Texture of upper and lower surfaces: Glabrous. Color of upper surface of young and mature foliage: 137B with 144D at base, slightly glaucous, venation indistinguishable. Color of lower surface of young and mature foliage: 137B to 137C with 144D at base, venation indistinguishable.

Flowering description:

*Flowering habit.*—'Savanna Lightning' is freely flowering under outdoor growing conditions with substantially continuous blooming from spring through autumn.

*Lastingness of individual umbel on the plant.*—Approximately 1 to 2 weeks.

Inflorescence description:

*General description.*—Type: Umbel, semi-spherical. Positioned above foliage. Subtended by two membranous bracts. Quantity of fully open umbels per plant: Approximately 1. Quantity of developing umbels per plant: Approximately: 0. Fragrance: None detected. Length or height: Approximately 2.5 cm. Width: Approximately 4.0 cm. Quantity of fully open flowers per inflorescence: Approximately 5.

*Scape.*—Strength: Strong. Shape in cross-section: Round, slightly flattened. Aspect: Erect to 45° angle. Length: Approximately 34.0 cm. Diameter: Approximately 2.0 mm. Texture: Glabrous, glaucous. Color: Closest to 146A with 144A.

Flower description:

*General description.*—Type: Single, apetalous. Shape: Salverform. Diameter: Approximately 1.9 cm. Depth: Approximately 1.1 cm.

*Bud.*—Rate of opening: Generally takes 3 to 4 days for bud to progress from first color to fully open flower.

*Bud just before opening.*—Shape: Obovate. Length: Approximately 1.1 cm. Width: Approximately 3.0 mm. Texture: Glabrous, glaucous. Color: NN155D.

*Tepals.*—Quantity: 6 lobed in 2 slightly imbricate whorls. Shape: Narrowly ovate. Appearance: Dull. Margin: Entire. Apex: Acute. Base: Fused. Length of outer tepals: Approximately 8.0 mm. Width of outer tepals: Approximately 4.0 mm. Length of inner tepals: Approximately 8.0 mm. Width of inner tepals: Approximately 3.0 mm. Texture of upper and lower surfaces: Glabrous. Color of upper surface when first and fully open: NN155D. Color of lower surface when first and fully open: NN155D.

*Corona.*—Quantity: 3 distinct scales located opposite inner lobes. Margin: Entire. Apex: Notched. Base: Fused. Length: Approximately 2.0 mm. Width at base (widest point): Approximately 1.0 mm. Texture of upper and lower surfaces: Glabrous. Color of upper and lower surfaces: 11B with a heavy overlay of 23A.

*Perianth tube.*—Length: Approximately 9.0 mm. Width: Approximately 3.0 mm. Texture: Glabrous. Color: NN155D at tube opening, transitioning through 145D in center to 144A at base.

*Pedicel.*—Strength: Strong. Aspect: Acute angle to horizontal. Length: Approximately 1.1 cm. Diameter: Less than 1.0 mm. Texture: Glabrous, glaucous. Color: 137A.

*Reproductive organs.*—Androecium: Quantity: 6 per flower, filaments adnate to perianth tube, anthers in 2 groups, upper group top of anther positioned 2.0 mm from tube opening and lower group top of anther positioned 4.0 mm from tube opening. Anther shape: Ovoid. Anther length: Approximately 1.0 mm. Anther color: 2B. Pollen amount: Abundant. Pollen color: 2A. Gynoecium: Pistil quantity: 1 per flower. Pistil length: Approximately 4.0 mm. Stigma shape: Capitate, papillate. Stigma length: Less than 1.0 mm. Stigma color: Colorless, translucent. Style length: Approximately 1.0 mm. Style color: Colorless, opaque. Ovary length: Approximately 3.0 mm. Ovary color: 145A.

Seed and fruit production: Neither seed nor fruit production has been observed.

Disease and pest resistance: Resistance to pathogens and pests common to *Tulbaghia* has not been observed.

What is claimed is:

1. A new and distinct cultivar of *Tulbaghia* plant named 'Savanna Lightning', substantially as herein illustrated and described.

* * * * *